United States Patent
Wisted et al.

[11] Patent Number: 5,897,779
[45] Date of Patent: Apr. 27, 1999

[54] SPIRAL WOUND EXTRACTION CARTRIDGE

[75] Inventors: Eric E. Wisted, Apple Valley; Susan H. Lundquist, White Bear Township, both of Minn.

[73] Assignee: Minnesota Mining and Manufacturing Company, St. Paul, Minn.

[21] Appl. No.: 08/791,205

[22] Filed: Feb. 13, 1997

[51] Int. Cl.⁶ ...................................................... B01D 61/00
[52] U.S. Cl. ................. 210/651; 210/502.1; 210/321.83; 210/321.74; 210/493.4; 210/493.1
[58] Field of Search .............................. 210/638, 321.74, 210/321.83, 493.4, 494.1, 651, 502.1

[56] References Cited

U.S. PATENT DOCUMENTS

| | | | |
|---|---|---|---|
| 4,033,878 | 7/1977 | Foreman et al. | 210/321.74 |
| 4,183,811 | 1/1980 | Walch et al. | 210/321.83 |
| 4,431,542 | 2/1984 | Dingfors et al. | 210/502.1 |
| 4,986,909 | 1/1991 | Rai et al. | 210/502.1 |
| 4,990,248 | 2/1991 | Brown et al. | 210/321.74 |
| 5,128,037 | 7/1992 | Pearl et al. | 210/321.74 |
| 5,279,742 | 1/1994 | Markell et al. | 210/502.1 |
| 5,700,375 | 12/1997 | Hagen et al. | 210/502.1 |

*Primary Examiner*—Ana Fortuna
*Attorney, Agent, or Firm*—William J. Bond

[57] ABSTRACT

A cartridge device for removing an analyte from a fluid comprises a hollow core, a sheet composite comprising a particulate-loaded porous membrane and optionally at least one reinforcing spacer sheet, the particulate being capable of binding the analyte, the sheet composite being formed into a spiral configuration about the core, wherein the sheet composite is wound around itself and wherein the windings of sheet composite are of sufficient tightness so that adjacent layers are essentially free of spaces therebetween, two end caps which are disposed over the core and the lateral ends of the spirally wound sheet composite, and means for securing the end caps to the core, the end caps also being secured to the lateral ends of the spirally wound sheet composite. A method for removing an analyte from a fluid comprises the steps of providing a spirally wound element of the invention and passing the fluid containing the analyte through the element essentially normal to a surface of the sheet composite so as to bind the analyte to the particulate of the particulate-loaded porous membrane, the method optionally including the step of eluting the bound analyte from the sheet composite.

21 Claims, 3 Drawing Sheets

SPIRAL WOUND EXTRACTION CARTRIDGE

The U.S. Government has certain rights in this invention under Department of Energy Contract No. DE-AR21-96MC33089.

FIELD OF THE INVENTION

The present invention relates to a spirally wound filter element for a cartridge for removing an analyte from a fluid, and a method of manufacturing and using the same.

BACKGROUND OF THE INVENTION

The use of filters for the removal of suspended particles from fluids is well known and has been extensively described in the literature. In general, these devices use size exclusion to remove contaminants. More particularly, a given filter which can comprise particles, webs, or papers, has pores within a particular size range. Particles larger than the pores are caught by the filter and removed from the fluid. Particles smaller than the pores may pass through the filter.

Unlike filtration, sorption relies on a chemical or physical interaction between the sorbing species and the species to be absorbed (i.e., the contaminant) in order to remove the latter from a fluid. (Accordingly, sorption can be used to remove dissolved as well as suspended species.) Sorption is most often performed in columns packed with porous granules. Leading from the exterior to the interior of these granules are pores containing what may be termed active sites, i.e., reactive groups bound to the granule or present on the surfaces thereof. Optimally, the distance from the exterior of the granule to the active site which the contaminant must travel should be as small as possible. One way to do this is to minimize the size of the granule. However, the minimum size of such granules is limited by the following factors: the size of the openings in the screen used to support the granules in the column and the pressure drop developed by fluids passing through the column. Therefore, column-packing granules have a minimum size below which column sorption becomes impractical.

A known device is a crepe paper filter element in a coiled configuration that has been described in U.S. Pat. No. 3,759,391. The crepe paper is folded into a V-shaped configuration and two adhesively attached spacer strips are described.

SUMMARY OF THE INVENTION

Briefly, this invention provides a device for removing an analyte from a fluid comprising:
a) a hollow core comprising a tubular structure having an internal cavity, an outer surface, fluid inlet openings from the outer surface into the cavity and a fluid outlet; and
b) a layered sheet composite comprising
1) a porous membrane comprising a fibrous sheet material having analyte-sorbing particles enmeshed therein capable of removing the analyte from the fluid; and
2) a porous reinforcing spacer sheet, the layered sheet being formed into a spiral configuration with the porous reinforcing spacer sheet being disposed over the outer surface and inlet openings of the core and being interposed between adjacent overlapping portions of the porous membrane
a) providing a device for removing an analyte from a fluid containing the analyte, the device comprising
1) a hollow core comprising a tubular structure having an internal cavity, an outer surface, fluid inlet openings from the outer surface into the cavity and a fluid outlet; and
2) a layered sheet composite comprising
i) a porous membrane comprising a fibrous sheet material having analyte-sorbing particles enmeshed therein capable of removing the analyte from the fluid; and
ii) a porous reinforcing spacer sheet, the layered sheet being formed into a spiral configuration with the porous reinforcing spacer sheet being disposed over the outer surface and inlet openings of the core and being interposed between adjacent overlapping portions of the porous membrane, and
b) passing the fluid containing the analyte through the spirally wound sheet composite essentially normal to a surface of the sheet composite so as to bind the analyte to the particulate of the particulate loaded porous membrane, and
c) optionally, eluting the bound analyte from said sheet composite with a stripping solution.

The sheet composite in its spiral (coiled) configuration provides a sorptive or reactive element comprising one or more particle-loaded membranes, one or several of which, optionally, and preferably, are interleaved by one or more reinforcing spacer sheets. When present, the reinforcing spacer sheet is essentially homogeneous and can be a separate adjacent layer or it can be partially embedded in the particle-loaded membrane. Preferably, it is a screen or scrim. Use of a separate reinforcing spacer sheet adjacent to the particle-loaded membrane is preferred because it can provide the membrane with mechanical strength and resistance to deformation when a pressure drop is applied across it. Use of such a reinforcing spacer sheet surprisingly contributes to lower back pressure, lower pressure drop, and increased extraction efficiency during the extraction process.

In this application:

"analyte" means a chemical substance (e.g., a complex, molecule, or ion) that is solvated in a fluid;

"bind" or "bound" means to sorb (or sorbed) or chemically react (or reacted) with an analyte;

"sorb" or "sorption" or "sorptive" means adsorption or absorption.

"screen" means a porous reinforcing material with a regular geometric pattern of threads which can be polymeric, glass, metallic, etc.;

"scrim" means a porous non-woven web, the fibers of which are not in a regular geometric pattern and which can be polymeric, glass, metallic, etc.;

"bed volume" means the total volume of the membrane in a cartridge;

"capacity at 50% breakthrough" means the total amount of analyte sorbed by the particle-loaded membrane at the point in time when the effluent contains 50% of the initial analyte input;

"partially embedded" (when used in connection with a reinforcing spacer means) means the reinforcing spacer means is (a) at least partially depressed in the membrane to which it has been pressure bonded so that the reinforced web, when viewed from an edge, shows only up to 95 percent, preferably up to 90 percent, more preferably up to 75 percent, and most preferably up to 50 percent, of the reinforcing means, and (b) at least partially mechanically entangled with the web;

"particles" and "particulate" are used interchangeably in this application;

"membrane" or "web" means a porous material which can be a fibrous nonwoven or woven sheet material, including a wet-laid web made by a paper making process from fibrous pulps, or it can be a solid (e.g. polymeric or cellulosic) sheet with pores therein; and "hydrocarbon" (when used in conjunction with binders) means an organic material that may contain heteroatoms (e.g., O, S, N, F, etc.) but derives at least 50% of its weight from hydrogen and carbon.

Preferably, the sheet composite is prepared as a layered construction with a reinforcing spacer sheet overlying a particle-loaded porous membrane. The layered construction is then spirally wound about a cartridge core and about itself and the end optionally is sealed against itself.

The spirally wound sheet composite of the invention without at least one reinforcing spacer sheet shows an advantage of greater capacity at 50% breakthrough and higher extraction efficiency compared to pleated cartridges.

Use of a reinforcing spacer sheet in the present invention spirally wound layered sheet composite provides the advantage of lower back pressure compared to spirally wound cartridges without reinforcing spacer sheet while exhibiting higher extraction efficiency.

DETAILED DESCRIPTION OF THE PREFERRED EMBODIMENTS

Figure 1:
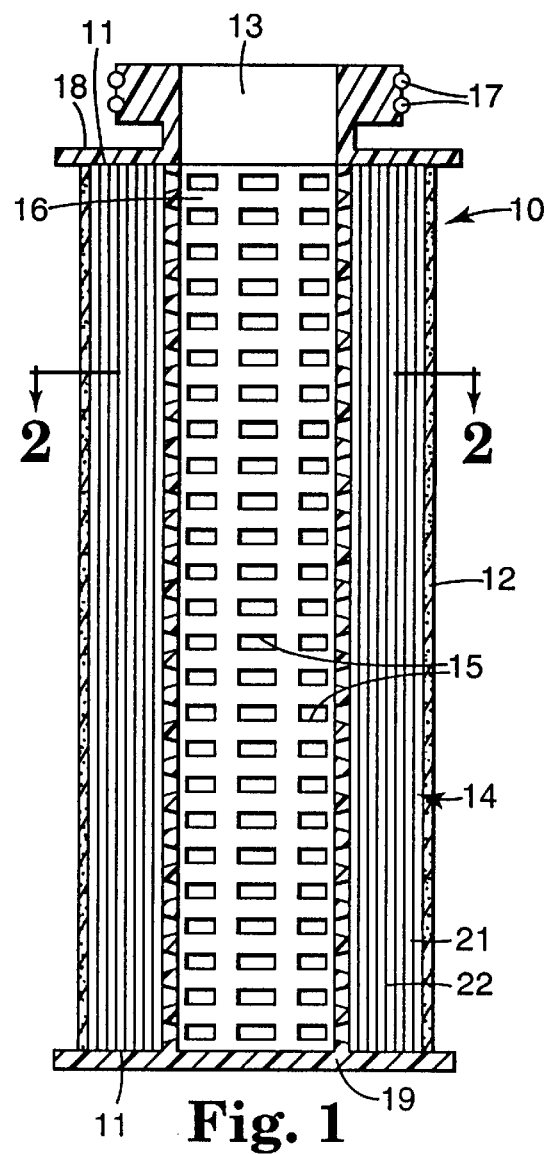
FIG. 1 is a cross-sectional view, showing one embodiment of a spirally wound cartridge device of the present invention comprising a reinforcing spacer sheet.

FIG. 1 shows a cross-sectional view of cartridge device 10 comprising layered sheet composite 14 which has been spirally wound. Cartridge device 10 includes hollow perforated core 16 having openings 15 therein, top end cap 18 having exit port 13 therein, and bottom end cap 19. Top end cap 18 comprises O-rings 17 which seal cartridge device 10 into a cartridge housing (not shown). The cartridge housing can be made of a polymeric or metallic material. Core 16 and end caps 18 and 19, which can be polymeric or metallic, preferably are constructed of a metal such as stainless steel or a polymer such as polypropylene or nylon. Where hollow core 16 and end caps 18 and 19 are constructed of a metal, they can be attached to one another adhesively, for example by an epoxy resin. Where each is polymeric, they can be attached adhesively or by fusion bonding. Depending on the method used to seal core 16 to end caps 18 and 19, the presence of small recesses or depressions (not shown) in end caps 18 and 19 (to receive core 16) may be desirable. O-rings 17 are attached to top end cap 18 before cartridge device 10 is inserted into a housing (not shown) and subjected to fluid flow. End caps 18 and 19 are secured (preferably by sealing or bonding) to lateral ends 11 of spirally wound layered sheet composite 14 and to hollow core 16 so that no fluid by-passes layered sheet composite 14 during an extraction process. In this embodiment fluid exits hollow core 16 through exit port 13 in top end cap 18. In other embodiments (not shown) fluid can exit hollow core 16 through both top end cap 18 and bottom end cap 19, where other means of attaching the cartridges device to the housing may be appropriate.

A typical cartridge housing that can be used in the present invention is commercially available from Memtec America Corp. (Timonium, Md.) under the designation Model LMO-VS-10503/4.

Layered sheet composite 14 includes particle-loaded porous membrane 21 with active particulate (not shown) entrapped therein, and reinforcing spacer sheet 22. Preferred embodiments of reinforcing spacer sheet 22 include screens, which can be metallic or polymeric, and scrims, i.e., non-woven, fibrous webs preferably made from materials such as nylon, polypropylene, and cellulose. Reinforcing spacer sheet 22 can lie adjacent to particle-loaded porous membrane 21 or it can be at least partially embedded in particle-loaded porous membrane 21. Particle-loaded porous membrane 21 preferably has a thickness in the range of 0.1 to 15 mm, more preferably in the range of 0.1 to 10 mm, and most preferably in the range of 0.1 to 5.0 mm. Both edges of reinforcing spacer sheet 22 and particle-loaded porous membrane 21 (spirally wound about core 16) optionally can be sealed, preferably adhesively, to the inner and outer surfaces of layered sheet composite 14. The method of making particle-loaded porous membrane 21 is described, for example, in U.S. Pat. Nos. 3,971,373, 5,071,610, 5,328,758, 5,026,456 and 5,082,720, which are incorporated herein by reference. Other methods of making particle-loaded membranes are discussed below. In this embodiment, reinforcing spacer sheet 22 can be a scrim comprising a nonwoven polypropylene web available from, for example, AMOCO Fabrics & Fibers Co. (Atlanta, Ga.). Any porous scrim or screen that is stable to the analyte-containing fluid can be used as a reinforcement means, however.

In other embodiments, reinforcing spacer sheet 22 can be Nitex™ 37 nylon (TETKO, Inc., Rolling Meadows, Ill.), Naltex™ LWS filtration netting (Nalle Plastics, Inc., Austin, Tex.), Monodier™ Nylon 475 and 850 screens (Industrial Fabrics Corp., Minneapolis, Minn.), Celestra™ and PBN II™ non-woven webs (Fiberweb, Inc., Pensacola, Fla.), Brookings™ non-woven webs (Minnesota Mining and Manufacturing Co., St. Paul, Minn.), Typar™ and 4dpf™ Straight non-woven webs, Reemay, Inc., Old Hickory, Tenn.), Coverstock™ non-woven webs (Bonar Fabrics, Greenville, S.C.), and RFX™ non-woven webs, AMOCO Fibers and Fabrics, Inc., Atlanta, Ga.).

The reinforcing separator sheet used in the composite article of preferred embodiments of the present invention is at least somewhat porous, preferably very porous (i.e., at least 50 percent voids), so as not to greatly interfere with the porosity of the membrane. This reinforcing spacer sheet can be at least partially embedded in the porous membrane. In such embodiments the porous membrane appears to actually attach to or become mechanically entangled with the reinforcing means.

Spirally wound layered sheet composite 14 is optionally enclosed within porous protective sheath 12, which can be metallic or polymeric, commercially available from a variety of sources. The protective sheath 12 can be tubular in shape and surrounds the exterior of spirally wound layer sheet composite 14. The sheath 12 helps to protect layered sheet composite 14 during handling and use. Any porous, preferably mesh-like, material can be used providing that the aforementioned protection is provided and it is stable to the analyte-containing fluid. Preferred materials include polymeric nets, especially those made of polypropylene, such as are available from Nalle Plastics, Inc. (Austin Tex.) and Conwed Plastics (Minneapolis, Minn.).

Embodiments of the present invention that do not comprise a reinforcing spacer sheet are made by methods essentially identical to those for the preferred embodiments that are described in detail herein except that there is no interleaved reinforcing spacer sheet in the spirally wound composite.

Active particulate useful in the present invention include any particulate that can be immobilized in any of a fibrillated polytetrafluoroethylene (PTFE) membrane, a woven or nonwoven membrane such as a melt blown mat, a wet-laid (pulp) membrane, or a solution-cast porous membrane, and that can bind the analytes of interest.

Representative examples of active particles that can be incorporated in the solid phase extraction sheet of the present invention include those that, by ion exchange, chelation, covalent bond formation, size exclusion, or sorption mechanisms, bind and remove molecules and/or ions from fluids in which they are dissolved or entrained. Particles that undergo chemical reactions including oxidation and/or reduction are a particularly useful class. Representative examples include silico titanates such as Ionsiv™ crystalline silico titanate (UOP, Mount Laurel, N.J.), sodium titanate (Allied Signal Corp., Chicago, Ill.), anion sorbers such as derivatized styrene divinylbenzene (Anex™ organic anion sorber, Sarasep Corp., Santa Clara, Calif.), cation sorbers such sulfonated styrene divinylbenzene (Diphonix™ organic cation sorber, Eichrom Industries, Chicago, Ill.), inorganic oxides such as silica, alumina, and zirconia, and derivatives thereof Useful derivatives include polymeric coatings and organic moieties (such as $C_{18}$ or $C_8$ alkyl chains, chelating ligands, and macrocyclic ligands) that are covalently bonded to an inorganic oxide particle, such as silica. For an overview of such particles and derivatized particles, see, e.g., U.S. Pat. Nos. 5,393,892, 5,334,326, 5,316,679, 5,273,660, 5,244,856, 5,190,661, 5,182,251, 5,179,213, 5,175,110, 5,173,470, 5,120,443, 5,084,430, 5,078,978, 5,071,819, 5,039,419, 4,996,277, 4,975,379, 4,960,882, 4,959,153, 4,952,321, and 4,943,375, the disclosures of which are incorporated herein by reference.

Other useful active particles include polymeric organic resins, such as styrene divinylbenzene and derivatives thereof. The particles can have ion exchange, chelation, or chiral separation properties. Hydrophobic zeolites such as those sold under the trade name Silicalit™ (UOP) are particularly useful in an aramid fiber sheet for isolating volatile organic compounds since both components are stable at high temperatures. Carbon (in either activated or unactivated form) can be useful as a sorptive particulate in certain applications. Hydrophobic molecular sieves can be useful to sorb organic materials such as pollutants. Alumina coated with elemental gold is a useful reactive particulate in certain oxidation-reduction reactions, and to isolate elemental mercury by amalgam formation. Chitin can also be a useful particle.

Inactive diluent particles that can be included in the SPE sheet include ferric oxide, inactive titanium dioxide, and the like. Such particles can have a positive affect on sheet strength and handleability.

Particulate material can be of regular (flat, spherical, cubic, rod- or fiber-like, etc.) or irregular shape. Average diameters (largest diameter)of useful particles are within the range of 0.1 to 150 $\mu$m, more preferably within the range of 1 to 100 $\mu$m, and most preferably within the range of 5 to 30 $\mu$m. The effective average diameter of the particles preferably is at least 125 times smaller than the uncalendered thickness of the sheet, more preferably at least 175 times smaller than the uncalendered thickness of the sheet, and most preferably at least 200 times smaller than the uncalendered thickness of the sheet. Such particulate can be incorporated directly into membrane 21. The membrane retains the enmeshed particulate, by entrapment or adhesion, within the matrix, and the enmeshed particles resist sloughing.

Because the capacity and efficiency of the SPE sheet depends on the amount of active particles included therein, high particle loading is desirable. The relative amount of particles in a given SPE sheet of the present invention is preferably at least about 50 percent (by weight), more preferably at least about 70 percent (by weight), and most preferably at least about 80 percent (by weight) up to about 97.5 percent (by weight). Preferably, a large plurality of these particles are active particles.

Particulate is generally distributed uniformly in membrane 21, and membranes which include combinations of particulate can be prepared. Alternatively, layers containing different particulate can be calendered into a single membrane with distinct strata of particulate. Such multilayer composites show minimal boundary mixing (between the various particulate) and retain good uniformity throughout each layer. Whether in a heterogeneous or homogenous form, this type of membrane can selectively bind one or more analytes to be removed from a fluid.

Regardless of the type or amount of the particles used in the solid phase extraction sheet of the present invention, they are preferably mechanically entrapped or entangled in the polymeric fibers of the porous polymeric pulp. In other words, the particles preferably are not covalently bonded to the fibers.

Membrane 21 can comprise active particulate in an amount of at least 10 percent (by weight), preferably comprises active particulate in an amount of at least 50 percent (by weight), and most preferably comprises active particulate in an amount of at least 80 percent (by weight). Membrane 21 can comprise particulate in an amount up to about 97.5 percent (by weight), although particulate amounts in the range of 85 to 90 percent (by weight) tend to produce more stable membranes. High active particulate loading is desirable to extend the sorptive capacity of membrane 21. Where cartridge device 10 is to be used in the removal of a metal from a solution, the particulate will preferentially bind that metal or a complex or salt thereof. In preferred embodiments, where various metal ions (both anions and cations) such as, for example, perrhenate, pertechnetate, perchromate, cesium, strontium, or lead, are to be removed from a fluid, derivatized styrene divinylbenzene particles (Anex™ resin, Sarasep Corp., Santa Clara, Calif.) can be used to remove anionic species from the water, and crystalline silico titanate particles (UOP, Mount Laurel, N.J.) can be used for the removal the cation species. Organic compounds such as polychlorinated biphenyl ("PCB's") and dioxins can be removed from contaminated water by using activated carbon.

Layered sheet composite 14 can be attached at one lateral end 11 to top end cap 18 and at the other lateral end 11 to bottom end cap 19 by any of a number of techniques as long as a fluid-impervious bond is achieved. Suitable techniques include adhesive attachment, solvent welding, spin welding, mechanical or thermomechanical attachment, and ultrasonic welding. This fluid-tight seal ensures that fluid flowing through cartridge device 10 must pass through layered sheet composite 14, particularly particle-loaded porous membrane 21. As fluid passes through porous membrane 21, active particulate entrapped therein preferentially binds the analyte to be removed. Typically, fluid enters cartridge device 10 through layered sheet composite 14 essentially normal to the outer surface of the spirally wound layered sheet composite and exits through the inner surface of layered sheet composite 14 and openings 15 in central core 16 and exit port 13 in the top end cap 18, although the opposite flow arrangement is also possible.

Figure 2:
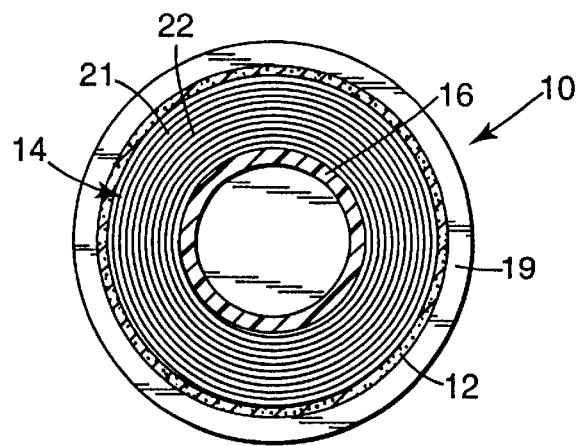
FIG. 2 is a cross-sectional view of the cartridge device of FIG. 1 taken along line 2—2.

FIG. 2 shows a cross-section of cartridge device 10 of FIG. 1 taken along line 2—2. Central core 16, adhesively attached to end caps 18 and 19, is surrounded by spirally wound sheet composite 14 comprising particle-loaded porous membrane 21 and reinforcing spacer sheet 22 shown merely as a dark line because it is relatively thin compared to the thickness of porous membrane 21. The outer edge of spirally wound layer composite sheet 14 can be connected to itself at a seal not shown. Fluid enters cartridge device 10 through spirally wound layered sheet composite 14 containing porous membrane 21 which has active particulate entrapped therein. Fluid passing through reinforcing spacer sheet 22 does so in a sectionally indifferent manner. In other words, fluid passes essentially equally through each portion of reinforcing spacer sheet 22. The spirally wound sheet composite 14 is optionally protected by protective mesh sheath 12.

If desired, additional layers of particle-loaded porous membranes and optional reinforcing spacer sheets can be used by stacking and then spirally winding (with each additional porous membrane optionally being separated from any previous particle-loaded porous membrane by at least one reinforcing spacer sheet) or butting in sequence different particle-loaded porous membranes and then spirally winding into a coil. These additional layers of particle-loaded porous membranes can contain active particulate that is selective for a different type of species than the particulate used in a first layered sheet composite. In this way, or in embodiments where more than one type of particulate is enmeshed in a membrane, a plurality of dissimilar species can be removed by one cartridge absorber device. A spirally-wound particle-loaded layered sheet composite including a reinforcing spacer sheet can be produced as follows:

A segment of active membrane is cut (length of the segment is analyte dependent). A section of reinforcing spacer sheet is next cut to a length that is longer by at least the length of the outer circumference of the core than the segment of active membrane. The reinforcing spacer sheet is laid out and the active membrane is placed on top of the reinforcing spacer sheet so that the extra reinforcing spacer material protrudes from both edges of the active membrane. The center core is placed on the leading edge of the reinforcing spacer sheet. A single wrap of the reinforcing spacer sheet is placed on the center core and the leading edge of the active membrane butted up to the core by placing the leading edge in the space between the reinforced spacer web on the core and that yet to be wrapped onto the core. The active membrane is rolled onto the center core, excess reinforcing spacer sheet is trimmed back so approximately one centimeter of the reinforcing spacer material protrudes past the trailing edge of the active membrane. The external seam is sealed with, for example, epoxy adhesive. The epoxy is allowed to cure. The two end caps are secured in place, to both edges of the layered composite sheet and to the ends of the hollow core, and the epoxy or other adhesive is allowed to cure overnight prior to using the cartridge.

Figure 3:
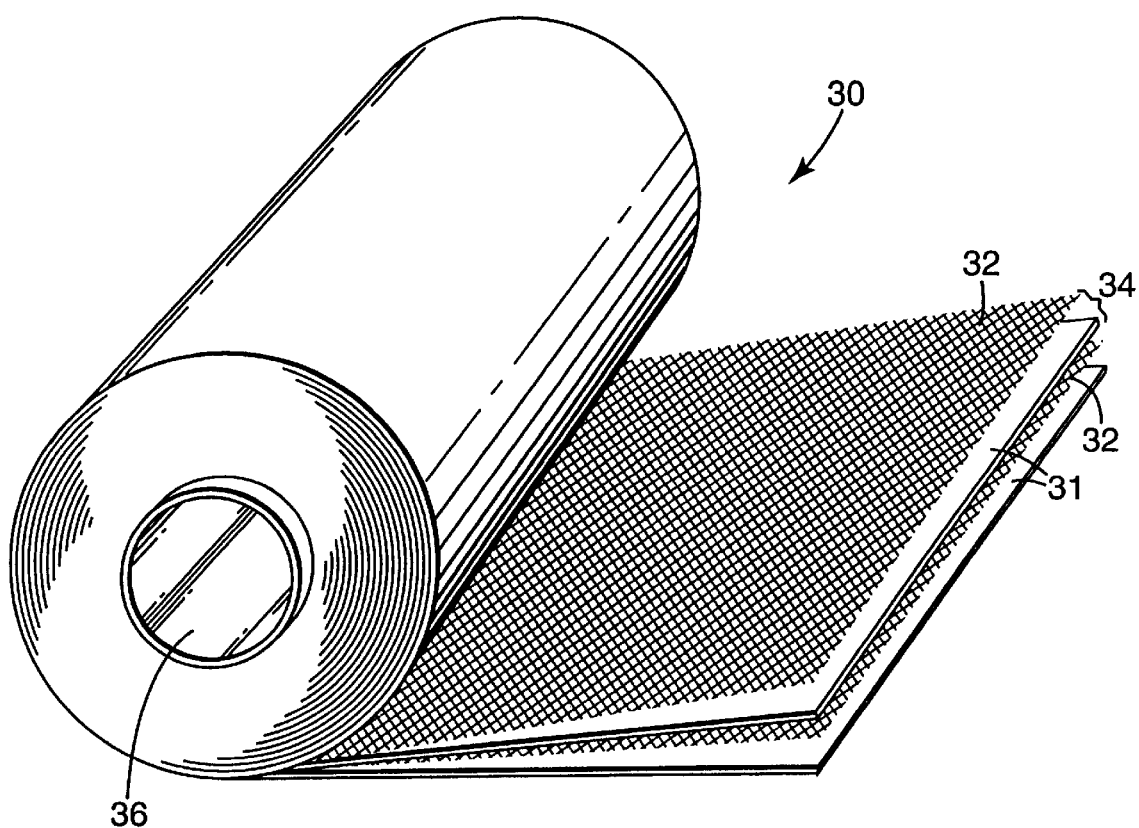
FIG. 3 is a perspective view of a spirally wound element of the present invention showing two layered sheet composites including reinforcing spacer sheets.

FIG. 3 shows a spirally wound layered sheet composite 30 of the present invention produced from a plurality of layered sheet composites 34, each layered sheet composite 34 comprising particle-loaded porous membrane 31 interleaved with reinforcing spacer sheet 32, the plurality of layered sheet composites 34 being wound about hollow core 36.

Figure 4:
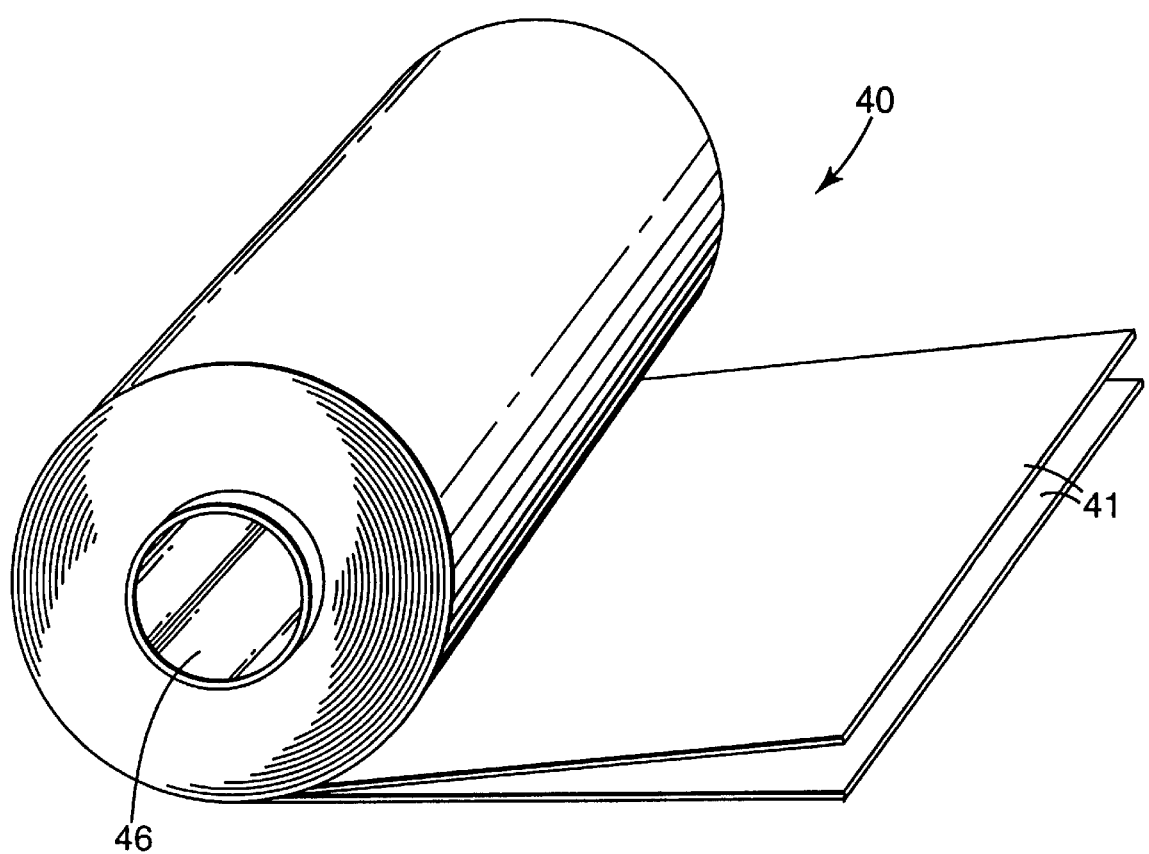
FIG. 4 is a perspective view of a spirally wound element of the present invention showing two sheet composites.

FIG. 4 shows a spirally wound element of the invention 40. Sheet composites 41 are wound together about hollow core 46. A single composite sheet 41 can be used when only one type of particulate is desired.

As just discussed, the particles in particle-loaded porous membranes useful in the invention can be different so as to remove different analytes from a fluid. The number of spiral windings and tightness of the winds of the sheet composite depends on the amount and type of active particles, and the nature of the contaminated fluid. Typically, 2 to 20 windings are used with all layers in contact with each other and preferably touching each other at a plurality of points. Spirally wound sheet composites of the invention can have any desired diameter depending upon the application. A particularly useful diameter for a spirally wound layered sheet composite of the invention is in the range 60 to 80 mm. Embossing of the sheet composite can be achieved prior to winding or can be inherent because of the optional scrim or screen pressing against the particle-loaded porous membrane, dependent upon the tightness of the windings. Embossing is not required. When no scrim or screen is present the windings are of sufficient tightness such that there is essentially no space between adjacent layers of sheet material.

In practice, flow rate of the fluid containing the analyte to be bound will vary depending on the nature of the binding particle, the binding rate of the analyte as well as the pressure built up in the device as a result of flow. Analytes that bind rapidly allow for higher fluid flow rates. Performance of the cartridge device can be determined by monitoring the concentration of the species to be bound at the inlet to and the outlet from the cartridge absorber.

Particulate to be used in a particular sheet will depend on the species to be bound. For example, where the species to be absorbed is an organic contaminant, a preferred particulate is activated carbon. When the carbon particulate has bound as much contaminant as possible, the cartridge absorber is advantageously easily replaced.

Where the bound species is of some value, it can be unbound from the binding particulate by eluting it with a stripping solution. In this process, the particle-loaded porous membrane is washed with a liquid that will regenerate the particle. This type of binding-stripping-regeneration process can be continued for a number of cycles. In other words, when one cartridge is fully loaded with the bound species, it can be replaced with another while the bound species is eluted from the first cartridge. When the second cartridge is fully loaded, the process is reversed. Using regenerable cartridge absorbing devices provides environmental and economic advantages.

In one embodiment, the membrane (web) can be fibrillated polytetrafluouroethylene (PTFE) having sorptive or reactive particulates enmeshed therein. In other embodiments of the present invention, the membrane (web) can comprise a solution-cast porous membrane or a non-woven, preferably polymeric macro- or microfibrous web in which fibers can be selected from the group consisting of polyamide, polyolefin, polyacrylamide, polyester, polyurethane, glass fiber, polyvinylhalide, or a combination thereof (If a combination of polymers is used, a bicomponent fiber can be obtained.) If polyvinylhalide is used, it preferably comprises fluorine of at most 75 percent (by weight) and more preferably of at most 65 percent (by weight). Addition of a surfactant to such webs may be desirable to increase the wettability of the component fibers.

More particularly, membranes useful in the present invention include:

1. Fibrillated PTFE webs

When the porous matrix is PTFE, the process for making webs as used in the present invention can be as disclosed, for example, in U.S. Pat. Nos. 4,153,661 and 5,071,610, which are incorporated herein by reference. Specifically, the PTFE composite article of the invention is prepared by mixing the particulate or combination of particulates employed, PTFE and lubricant, until a uniform mixture is obtained. PTFE and lubricant can be added as a PTFE resin emulsion which is commercially available from DuPont (Wilmington, Del.). It has been found that to optimize separation techniques in the resultant article, lubricant in the mixture, or subsequently added lubricant, i.e., water or water-based solvent or organic solvent, should be present sufficient to be near or to exceed the lubricant sorptive capacity of the particles preferably by at least 3 weight percent up to 200 weight percent. This range can be optimized for obtaining the desired mean pore sizes for different types of ion sorbing particles and for the different types of separations to be performed. PTFE fibrils can have a diameter in the range of 0.025 to 0.5 $\mu$m and an average diameter less than 0.5 $\mu$m.

Useful lubricants as well as blending, mixing, and calendering procedures are disclosed, for example, in U.S. Pat. Nos. 4,153,661 and 5,071,610, which are incorporated herein by reference for these procedures.

2. Macrofibers

Macrofibrous webs can comprise thermoplastic, melt-extruded, large-diameter fibers which have been mechanically-calendered, air-laid, or spunbonded. These fibers have average diameters in the general range of 50 $\mu$m to 1000 $\mu$m.

Such non-woven webs with large-diameter fibers can be prepared by a spunbond process which is well-known in the art. (See, e.g., U.S. Pat. Nos. 3,338,992, 3,509,009, and 3,528,129, which are incorporated herein by reference for the process.) As described in these references, a post-fiber spinning web-consolidation step (i.e., calendering) is required to produce a self-supporting web. Spunbonded webs are commercially available from, for example, AMOCO, Inc. (Naperville, Ill.).

Non-woven webs made from large-diameter staple fibers can also be formed on carding or air-laid machines (such as a Rando-Webber™, Model 12BS made by Rando Machine Corp., Macedon, N.Y.), as is well known in the art. See, e.g., U.S. Pat. Nos. 4,437,271, 4,893,439, 5,030,496, and 5,082,720, the processes of which are incorporated herein by reference.

A binder is normally used to produce self-supporting webs prepared by the air-laying and carding processes and is optional where the spunbond process is used. Such binders can take the form of resins which are applied after web formation or of binder fibers which are incorporated into the web during the air laying process. Examples of such resins include phenolic resins and polyurethanes. Examples of common binder fibers include adhesive-only type fibers such as Kodel™ 43UD (Eastman Chemical Products, Kingsport, Tenn.) and bicomponent fibers, which are available in either side-by-side form (e.g., Chisso ES Fibers, Chisso Corp., Osaka, Japan) or sheath-core form (e.g., Melty™ Fiber Type 4080, Unitika Ltd., Osaka, Japan). Application of heat and/or radiation to the web "cures" either type of binder system and consolidates the web.

Generally speaking, non-woven webs comprising macrofibers have relatively large voids, preferably having a mean pore size in the range of 5.0 to 50 micrometers. Therefore, such webs have low capture efficiency of small-diameter particulate (sorptive or reactive supports) which is introduced into the web. Nevertheless, particulate can be incorporated into the non-woven webs by at least four means. First, where relatively large particulate is to be used, it can be added directly to the web, which is then calendered to actually enmesh the particulate in the web (much like the PTFE webs described previously). Second, particulate can be incorporated into the primary binder (discussed above) which is applied to the non-woven web. Curing of this binder adhesively attaches the particulate to the web. Third, a secondary binder can be introduced into the web. Once the particulate is added to the web, the secondary binder is cured (independent of the primary system) to adhesively incorporate the particulate into the web. Fourth, where a binder fiber has been introduced into the web during the air laying or carding process, such a fiber can be heated above its softening temperature. This adhesively captures particulate which is introduced into the web.

Of these methods involving non-PJTFE macrofibers, those using a binder are generally the most effective in capturing particulate. Adhesive levels which will promote point contact adhesion are preferred.

Once the particulate (sorptive or reactive supports) has been added, the loaded webs are typically further consolidated by, for example, a calendering process. This further enmeshes the particulate within the web structure.

Webs comprising larger diameter fibers (i.e., fibers which have average diameters between 50 $\mu$m and 1000 $\mu$m) have relatively high flow rates because they have a relatively large mean void size.

3. Microfibers

When the fibrous web comprises non-woven microfibers, those microfibers can provide thermoplastic, melt-blown polymeric materials having active particulate dispersed therein. Preferred polymeric materials include such polyolefins as polypropylene and polyethylene, preferably further comprising a surfactant, as described in, for example, U.S. Pat. No. 4,933,229, the process of which is incorporated herein by reference. Alternatively, surfactant can be applied to a blown microfibrous (BMF) web subsequent to web formation. Particulate can be incorporated into BMF webs as described in U.S. Pat. No. 3,971,373, the process of which is incorporated herein by reference. Glass and ceramic nonwoven webs are known and particles can be incorporated in such webs as is known in the art; see, for example, WO 93/01494, which is incorporated herein by reference.

Microfibrous webs of the present invention have average fiber diameters up to 50 $\mu$m, preferably from 2 $\mu$m to 25 $\mu$m, and most preferably from 3 $\mu$m to 10 $\mu$m. Because the void sizes in such webs range from 0.1 $\mu$m to 10 $\mu$m, preferably from 0.5 $\mu$m to 5 $\mu$m, flow through these webs is not as great as is flow through the macroporous webs described above.

In this embodiment of the present invention, the particle-loaded fibrous article, which preferably can be a microfibrous article, can be compressed to increase its density and decrease interstitial porosity and comprises in the range of 30 to 70 volume percent fibers and particulate, preferably 40 to 60 volume percent fibers and particulate, and 70 to 30 volume percent air, preferably 60 to 40 volume percent air.

In general, pressed sheet-like articles are at least 20 percent, preferably 40 percent, more preferably 50 percent, and most preferably 75 percent reduced in thickness compared to unpressed articles. The article comprises pores having a mean pore size in the range of 0.1 to 10 micrometers, preferably 0.5 to 5 micrometers.

Blown fibrous webs are characterized by an extreme entanglement of fibers, which provides coherency and strength to an article and also adapts the web to contain and retain particulate matter. The aspect ratio (ratio of length to diameter) of blown fibers approaches infinity, though the fibers have been reported to be discontinuous. The fibers are long and entangled sufficiently so that it is generally impossible to remove one complete fiber from the mass of fibers or to trace one fiber from beginning to end.

4. Solution-Cast Porous Membranes

Solution-cast porous membranes can be provided by methods known in the art. Such polymeric porous membranes can be, for example, polyolefin, including PTFE and polypropylene, and polyamide, polyester, polyvinyl acetate, and polyvinyl chloride fibers. Membranes that include ion sorbing particles have sufficient porosity to allow passage of fluids.

5. Fibrous Pulps

When the porous matrix is a polymer pulp, sheet materials can be prepared by dispersing the polymer pulp(s), generally with particulate, preferably using a blender, in the presence of a suitable liquid, preferably water or water-miscible organic solvent such as alcohol or water-alcohol. The dispersion is poured through a fine screen preferably having pores of about 0.14 mm (100 mesh) to provide a wet sheet, which can then be pressed to remove additional liquid. The sheet is then dried, preferably by heating, to provide a dry sheet preferably having an average thickness in the range of about 0.1 mm to less than 10 mm, more preferably 0.2 mm to 9 mm, most preferably 0.3 mm to 5 mm, and even more preferably 0.4 mm to 3 mm. Up to 100 percent of the liquid can be removed, preferably up to 90 percent. Calendering can be used to provide additional pressing or fusing, when desired. This general method is provided in U.S. Pat. No. 5,026,456, which is incorporated herein by reference. The sheet resembles porous, unglazed paper that may have color, depending upon its components.

In a preferred embodiment, the sheet material for removing one or more chemical species dissolved or entrained in a fluid comprises a porous polymeric pulp comprising fibers, at least 75% of the fibers having a length of at least about 4 mm; from about 3 to about 7 weight percent of a polymeric hydrocarbon binder; and particles entrapped in said pulp, some of the particles exhibiting at least one of reactive and sorptive properties toward the chemical species, the particles being present in an amount such that the weight ratio of particles to binder is at least 13:1; the sheet having an average uncalendered thickness of up to about 5 mm, a basis weight of from about 600 to about 2000 g/m$^2$, and an apparent density of at least about 0.35 g/cm$^3$.

Generally, the fibers that make up the porous polymeric pulp of the SPE sheet of the present invention can be any pulpable fiber (i.e., any fiber that can be made into a porous pulp). Preferred fibers are those that are stable to radiation and/or to a variety of pHs, especially very high pHs (e.g., pH=14) and very low pHs (e.g., pH=1). Examples include polyamide fibers and those polyolefin fibers that can be formed into a pulp including, but not limited to, polyethylene and polypropylene. Aromatic polyamide fibers and aramid fibers are particularly preferred when stability to both radiation and highly caustic fluids is desired. Examples of useful aromatic polyamide fibers are those of the nylon family.

Suitable pulps for providing the sheet materials of the present invention include aramid pulps, preferably poly(p-phenyleneterephthalamide) (Kevlar™, Dupont) and polyacrylonitrile (PAN) and derivatives thereof Kevlar™ fiber pulps are commercially available in three grades based on the length of the fibers that make up the pulp. Blends with polyolefin pulps, such as at least one of polypropylene and polyethylene, can be used to optimize the physical and sorptive properties of the sheet materials. Ratios of aramid pulps to polyolefin pulps can be in the range of 1 to 100 weight percent to 99 to 0 weight percent, preferably 10 to 90 weight percent to 90 to 10 weight percent.

Regardless of the type of fiber(s) chosen to make up the pulp, the relative amount of fiber in the resulting SPE sheet (when dried) ranges from about 12.5 percent to about 30 percent (by weight), preferably from about 15 percent to 25 percent (by weight).

Preferably, when heavy metal ions are to be removed, fibrous SPE sheets useful in the invention comprise polymeric pulps, at least one binder, and ion exchange or chelating materials. A binder is used to add cohesive strength to the fibrous SPE sheet once it is formed by any of a number of common wet-laid (e.g., paper-making) processes.

Useful binders in the SPE sheet of the present invention are those materials that are stable over a range of pHs (especially high pHs) and that exhibit little or no interaction (i.e., chemical reaction) with either the fibers of the pulp or the particles entrapped therein. Polymeric hydrocarbon materials, originally in the form of latexes, have been found to be especially useful. Common examples of useful binders include, but are not limited to, natural rubbers, neoprene, styrene-butadiene copolymer, acrylate resins, and polyvinyl acetate. Preferred binders include neoprene and styrene-butadiene copolymer. Regardless of the type of binder used, the relative amount of binder in the resulting SPE sheet (when dried) is about 3 percent to about 7 percent by weight, preferably about 5 percent. The preferred amount has been found to provide sheets with nearly the same physical integrity as sheets that include about 7 percent binder while allowing for as great a particle loading as possible. It may be desirable to add a surfactant to the fibrous pulp, preferably in small amounts up to about 0.25 weight percent of the composite.

The weight percentage of particles in the resulting SPE sheet is at least 13 times greater than the weight percentage of binder, preferably at least 14 times greater than the weight percentage of binder, more preferably at least 15 times greater than the weight percentage of binder. Weight ratios of particles to binder can range up to about 28:1 where the minimum amount of binder (i.e., 3 weight percent) is used.

Regardless of the type or amount of the particles used in the SPE sheet of the present invention, they are mechanically entrapped or entangled in the polymeric fibers of the porous polymeric pulp. In other words, the particles preferably are not covalently bonded to the fibers.

The SPE sheet of the present invention can also include one or more adjuvants. Useful adjuvants include those substances that act as process aids and those substances that act to enhance the overall performance of the resulting SPE sheet. Examples of the former category include sodium aluminate and aluminum sulfate (commonly known as alum), which help to precipitate binder into the pulp, and dispersants or surfactants such as Tamol™ 850 dispersant (Rohm & Haas Co.; Philadelphia, Pa.). Examples of the latter category include crosslinking agents, such as zinc oxide, for certain binders, such as neoprene. When used, relative amounts of such adjuvants range from more than zero up to about 0.5% (by wt.), although their amounts are preferably kept as low as possible so as not to take away from the amount of particles that can be added.

Desirably, the average pore size of the uniformly porous sheet material can be in the range of 0.1 to 10 μm. Void volumes in the range of 20 to 80 percent can be useful, preferably 40 to 60 percent. Porosity of the sheet materials prepared from polymer pulp can be modified (increased) by including adjuvant hydrophilic or hydrophobic fibers, such as polyacrylonitrile, polypropylene or polyethylene fibers of larger diameter or stiffness which can be added to the mixture to be blended. Fibers can have an average size (diameter) of up to 20 μm, and preferably at least 75 percent by weight of fibers have an average length of at least about 4 mm; preferably any adjuvant fibers added, for example, to control porosity, are non-sorptive.

Details of the method of making the spiral wound filter element of the invention are given in the Examples, below.

The method of the present invention can be used for a variety of purposes including the removal of heavy metals from a body of water or an organic liquid, and the removal of environmental contaminants from air or a liquid. The analytes can be metal ions or organic compounds including residues of fuels, explosives, drugs, and pesticides. The cartridge of the present invention allows for the collection of an analyte of interest or value.

Objects and advantages of this invention are further illustrated by the following examples. The particular materials and amounts thereof, as well as other conditions and details, recited in these examples should not be used to unduly limit this invention.

EXAMPLES:

Example 1.

A. Pleated cartridge (comparative). To an agitated slurry of 10 g Kevlar™ 1F306 dried aramid fiber pulp, (E. I. Dupont Inc., Wilmington, Del. 19898) and 2500 ml water in a Waring blender was added 0.25 g Tamol™ 850 dispersant Rohm and Haas, Philadelphia, Pa.). After blending at a low speed setting for 30 seconds, 113.3 g of a 33% (by wt.) aqueous slurry of particles of Calgon™—PCB Grade Carbon (Keystone Filler and MFG Co, Muncy, Pa. 17756) was added with continued blending. Next, 6.25 g (2.5 g dry weight) Goodrite™ 1800×73 styrene-butadiene latex binder slurry (B.F. Goodrich Co.; Cleveland, Ohio), was added and blending was continued for 15 seconds at a low speed. To this mixture was added a solution of 25 g of a 25% by weight solution of alum in water, and blending was continued as the binder precipitated onto the pulp and particulate. A handsheet was prepared from the mixture and pressed for 5 minutes at 620 kPa. The method of manufacturing the pleated cartridge is described in patent application U.S. Ser. No. 08/590,978, which is incorporated herein by reference for the method of producing vertically pleated cartridges.

The active membrane as previously described was trimmed to a width of 22 cm and vertically pleated on a Rabovsky pleater (Gerard Daniel & Co., Inc., New Rochelle, N.Y.). The pleated sheet was longitudinally sealed with DP - 100™ quick-setting epoxy resin (3M; St. Paul, Minn.). A central core and one end cap of a filter cartridge housing (Arcor Inc.; Chicago, Ill.) were placed on a stand, and the end cap was covered with epoxy resin. The pleated reinforced sheet was placed over the cylinder. The end of the sheet was completely immersed in the aforementioned epoxy. Naltex™ 3408 (Nalle Plastics, Inc.) protective netting in tubular form was slid over the pleated sheet. The other end cap was placed over the pleated sheet and netting which were then sealed into both end caps with epoxy.

B. A spirally wound cartridge (without scrim) was fabricated in the following manner: (Specific cartridge specifications are given at the end of this Example.)

A segment of active membrane was prepared as previously described was cut to length (see below). The center core (Arcor Inc.; Chicago, Ill.) was placed on the leading edge of the active membrane. The active membrane was rolled onto the center core. The external seam was sealed with epoxy resin which was allowed to cure for a minimum of 10 minutes prior to proceeding with cartridge fabrication. Epoxy resin was used to seal the two end caps (Arcor Inc.; Chicago, Ill.) in place and the resin was allowed to cure overnight prior to using the cartridge.

Cartridge Characteristics

| | |
|---|---|
| active particle | Calgon - PCB Grade Carbon, Keystone Filler and Mfg. Co., Muncy, PA 17756 |
| membrane thickness | 1.3 mm |
| linear membrane length | 254 cm |
| membrane width | 22 cm |
| total carbon content | 290 grams |
| water extraction conditions | |
| flow rate across cartridge | 3.8 L/min |
| target analyte | 2-nitrophenol |
| analyte feed concentration | 10 ppm |
| See Table 1, below, for data. | |

Example 2.

The method of making the active membrane was as described in Example 1. In the formulation instead of Calgon-PCB Grade Carbon (Keystone Filler and Mfg. Co., Muncy, Pa. 17756) an aqueous slurry of SuperLig™ 304 (IBC Advanced Technologies Inc., American Fork, Utah.) 320 g of 6.25% (by wt.) was used.

Basic cartridge fabrication was performed as described in Example 1, i.e., a pleated cartridge (comparative) and a spirally wound cartridge without scrim were prepared. The only modification was the membrane width was cut to 16 cm instead of 22 cm.

Cartridge Characteristics

| | |
|---|---|
| active particle | SuperLig ™ 304 |
| membrane thickness | 1.5 mm |
| linear membrane length | 84.0 cm |
| membrane width | 16 cm |
| total SuperLig ™ 304 content | 100 grams |
| water extraction conditions | |
| flow rate across cartridge | 1.1 L/min |
| target analyte | $Cu^{+2}$ |
| analyte feed concentration | 20 ppm |
| See Table 1, below, for data. | |

Example 3.

The method of making the active membrane was as described in Example 1.

The spiral cartridge without reinforcing spacer sheet was described in Example 1 and fabrication of the spiral cartridge with reinforcing spacer sheet (Naltex™ LWS filtration netting (Nalle Plastics Inc., Austin, Tex.)) is described as follows: (Specific cartridge specifications are given at the end of this Example.)

A segment of active membrane was cut to length. A section of reinforcing spacer sheet was next cut to length that was longer than the segment of active membrane. The reinforcing spacer sheet was laid out and the active membrane was placed on top of the reinforcing spacer sheet so that the extra reinforcing spacer material protruded from both edges of the active membrane. The center core of the cartridge housing (Arcor Inc.; Chicago, Ill.) was placed on the leading edge of the reinforcing spacer sheet. A single wrap of the reinforcing spacer sheet was placed on the center core and the leading edge of the active membrane butted up to the core. The active membrane was rolled onto the center core. Excess reinforcing spacer sheet was trimmed back so approximately one centimeter of the reinforcing spacer material protruded past the trailing edge of the active membrane. The external seam was sealed with epoxy resin and the epoxy was allowed to cure for a minimum of 10 minutes. Epoxy resin was used to seal the two end caps (Arcor Inc.; Chicago, Ill.) in place and the epoxy was allowed to cure overnight prior to using the cartridge.

| Cartridge Characteristics | |
| --- | --- |
| active particle | Calgon - PCB Grade Carbon |
| membrane thickness | 1.3 mm |
| linear membrane length | 254 cm |
| membrane width | 22 cm |
| total carbon content | 290 grams |
| water extraction conditions | |
| flow rate across cartridge | 3.8 L/min |
| target analyte | 2-nitrophenol |
| analyte feed concentration | 10 ppm |
| See Table 1, below, for data. | |

Example 4.

The method of making the active membrane was as described in Example 1. In the formulation Calgon-PCB Grade Carbon (Keystone Filler and Mfg. Co., Muncy, Pa. 17756) was replaced with Anex™ particles (Sarasep Inc., Santa Clara, Calif. 95054) 30 g.

Cartridge fabrication, spirally wound, without scrim and with scrim, was described in Examples 1 and 3.

| Cartridge Characteristics | |
| --- | --- |
| active particle | Anex |
| membrane thickness | 3.0 mm |
| linear membrane length | 38.1 cm |
| membrane width | 16 cm |
| total Anex content | 58.4 grams |
| water extraction conditions | |
| flow rate across cartridge | 3.8 L/min |
| target analyte | $ReO_4^{-1}$ |
| analyte feed concentration | 2.5 ppm |
| See Table 1, below, for data. | |

Example 5.

The method of making the active membrane was as described in Example 1. In the formulation Calgon-PCB Grade Carbon (Keystone Filler and Mfg. Co., Muncy, Pa.) was replaced with potassium cobalt hexacyanoferrate (KCoHex™ manufactured as described in U.S. Pat. No. 3,296,123) 22.5 g.

Cartridge fabrication, spirally wound, without scrim and with scrim, was described in Examples 1 and 3.

| Cartridge Characteristics | |
| --- | --- |
| active particle | KCoHex |
| membrane thickness | 1.4 mm |
| linear membrane length | 124.5 cm |
| membrane width | 16 cm |
| total KCoHex content | 157.5 grams |
| water extraction conditions | |
| flow rate across cartridge | 3.8 L/min |
| target analyte | $Cs^{+1}$ |
| analyte feed concentration | 3.0 ppm |
| See Table 1, below, for data. | |

Example 6.

The method of making the active membrane was as described in Example 1. In the formulation, Calgon-PCB Grade Carbon (Keystone Filler and Mfg. Co., Muncy, Pa.) was replaced with mixed salts of titanium aluminosilicate (ATS particles, Engelhard Inc., Seneca, S.C. 29678) 37.5 g.

Cartridge fabrication, spirally wound, without scrim, and with scrim, was described in Examples 1 and 3.

| Cartridge Characteristics | |
| --- | --- |
| active particle | ATS, Engelhard Inc., Seneca, SC 29678 |
| membrane thickness | 2.2 mm |
| linear membrane length | 71.1 cm |
| membrane width | 16 cm |
| total ATS content | 175.2 grams |
| water extraction conditions | |
| flow rate across cartridge | 1.8 L/min |
| target analyte | $Sr^{+2}$ |
| analyte feed concentration | 0.3 ppm |
| See Table 1, below, for data. | |

Example 7.

The method of making the active membrane was as described in Example 1. In the formulation Calgon-PCB Grade Carbon Keystone Filler and Mfg. Co., Muncy, Pa. 17756) was replaced with ATS particle (Engelhard Inc., Seneca, S.C. 29678) 37.5 g and Kevlar™ 1F306 dried aramid fiber pulp, (E. I. Dupont Inc., Wilmington, Del. 19898) with high density polyethylene pulp, (Microfiber Inc., Johnson City, Tenn.) 10 g.

Cartridge fabrication, spirally wound, with scrim, was prepared as in Example 3.

| Cartridge Characteristics | |
| --- | --- |
| active particle | ATS, Engelhard Inc., Seneca, SC 29678 |
| membrane thickness | 2.2 mm |
| linear membrane length | 71.1 cm |
| membrane width | 16 cm |
| total ATS content | 175 grams |
| water extraction conditions | |
| flow rate across cartridge | 3.8 L/min |
| target analyte | $Sr^{+2}$ |
| analyte feed concentration | 0.3 ppm |
| See Table 1, below, for data. | |

Example 8.

The method of making the active membrane was as described in U.S. Pat. No. 5,071,610 Example 1.

In this case we carefully controlled the level of lubricant (1 part water/1 part isopropyl alcohol), to produce the membrane.

More particularly, ten grams of Anex particle (Sarasep Inc., Santa Clara, Calif. 95054) was placed in a 100 ml beaker. 1.6 grams of polytetrafluoroethylene (PTFE) resin emulsion (Teflon™ 30B, E. I. Dupont, Inc., Wilmington, Del.) was added stepwise in three portions with intermittent vigorous stirring. 10.5 gram of lubricant was added stepwise in three portions with intermittent vigorous stirring. After these ingredients had thoroughly mixed, a semi-coherent material was formed with enough physical integrity to allow the entire contents of the beaker to be removed as a single mass. The above mass was passed between two rollers kept at 50° C. and spaced about 0.5 cm apart to give a strip of cohesive material. The resulting strip was folded to three thicknesses and then passed through the rollers after a 90 degree rotation from the previous pass. The cyclic process of folding and re-rolling in the direction 90° from the direction of the previous pass was repeated multiple times to give a tough, strong, flat piece of material. The material was then calendered along the long axis via a series of roller passes with roller spacing adjusted to successively smaller distances apart to give a continuous ribbon. The ribbon was folded to give a multi-layer piece which was then calendered as before along the axis 90° from the calandering direction used previously. The calendered sheet of material was then allowed to dry in air for 48 hours.

A spirally wound cartridge without reinforcing spacer sheet was fabricated as described in Example 1 and a spiral cartridge with reinforcing spacer sheet was fabricated as described in Example 3.

| Cartridge Characteristics | |
|---|---|
| active particle | Anex, Sarasep Inc., Santa Clara, CA 95054 |
| membrane thickness | 0.5 mm |
| linear membrane length | 63.5 cmm |
| membrane width | 22 cm |
| total Anex content | 25.7 grams |
| water extraction conditions | |
| flow rate across cartridge | 0.95 L/min |
| target analyte | $Cr_2O_4^{-2}$ |
| analyte feed concentration | 10 ppm |
| See Table 1, below, for data. | |

Example 9.

The method of making an active membrane was as described in Example 8, except Anex particle (Sarasep Inc., Santa Clara, Calif. 95054) was replaced with $C_{18}$ bonded silica, (Varian, Inc., Harbor City, Calif.) 10 g.

Cartridge fabrication, spirally wound, without scrim, and with scrim, was as described in Examples 1 and 3.

| Cartridge Characteristics | |
|---|---|
| active particle | $C_{18}$ bonded silica |
| membrane thickness | 0.7 mm |
| linear membrane length | 66.0 cm |
| membrane width | 22 cm |
| total $C_{18}$ bonded silica content | 58.8 grams |

| water extraction conditions | |
|---|---|
| flow rate across cartridge | 1.9 L/min |
| target analyte | 2-nitrophenol |
| analyte feed concentration | 10 ppm |
| See Table 1, below, for data. | |

Example 10.

The method of making the active membrane was as described in U.S. Pat. No. 5,328,758, Example 1.

A blown microfiber sheet—like article was prepared from polypropylene type 34950™ (Exxon Corp., Baytown, Tex.) using conventional melt blowing apparatus as described in the patent reference. The particles in this example were Darco™- G60 Carbon (Norit Americas Inc., Atlanta, Ga. 30338). The particle loaded microfiber article had a weight of 230 g/m², for a loading percentage of 64% by weight, and a thickness of approximately 0.4 mm.

Cartridge fabrication, spirally wound without scrim, and with scrim, was as described in Examples 1 and 3.

| Cartridge Characteristics | |
|---|---|
| active particle | Darco-G60 Carbon |
| membrane thickness | 0.4 mm |
| linear membrane length | 172.7 cm |
| membrane width | 22 cm |
| total carbon content | 8.0 grams |
| water extraction conditions | |
| flow rate across cartridge | 1.9 L/min |
| target analyte | 2-nitrophenol |
| analyte feed concentration: | 10 ppm |
| See Table 1, below, for data. | |

Example 11.

The method of making the active membrane, spirally wound, without scrim, and with scrim, was as described in Example 10. Darco-G60 Carbon Norit Americas Inc., Atlanta, Ga. 30338) was replaced with ATS particle (Englhard Inc., Seneca, S.C. 29678). The particle loaded microfiber article had a weight of 215 g/m², for a loading percentage of 86% by weight, and a thickness of approximately 0.4 mm.

| Cartridge Characteristics | |
|---|---|
| active particle | ATS, Englhard Inc., Seneca, SC 29678 |
| membrane thickness | 0.4 mm |
| linear membrane length | 106.6 cm |
| membrane width | 22 cm |
| total ATS content | 42.6 grams |
| water extraction conditions | |
| flow rate across cartridge | 1.9 L/min |
| target analyte | $Sr^{+2}$ |
| analyte feed concentration | 3.0 ppm |
| See Table 1, below, for data. | |

Example 12.

In this Example, a single cartridge was constructed out of two active membranes containing different particles: ATS particles (Engelhard Inc., Seneca, S.C. 29678) 39 g and Anex Particles (Sarasep Inc., Santa Clara, Calif. 95054) 31.0 g. The method of making the active membrane was as described in Example 1.

The spiral cartridge with reinforcing spacer sheet (Naltex LWS filtration netting, Nalle Plastics Inc., Austin, Tex.)) was fabricated in the following manner: (Specific cartridge specifications are given at the end of this Example.)

A segment of both active membranes were cut to length. A section of reinforcing spacer sheet was next cut to length that was longer than the combined lengths of both segments of active membranes. The reinforcing spacer sheet was laid flat and both active membranes were placed on top of the reinforcing spacer sheet so that the leading edge of the second active membrane was butted up tight to the trailing edge of the first active membrane. The active membranes were positioned so the extra reinforcing spacer sheet protruded from the leading edge of the first membrane and the trailing edge of the second active membrane. The center core of one housing cartridge (Arcor Inc., Chicago, Ill.) was placed on the leading edge of the reinforcing spacer sheet. A single wrap of the reinforcing spacer sheet was placed on the center core and the leading edge of the first active membrane butted up to the core and both active membranes were rolled onto the center core. The excess reinforcing spacer sheet was trimmed back so approximately one centimeter of the reinforcing spacer sheet protruded past the trailing edge of the second active membrane. The external seam was sealed with epoxy adhesive and the epoxy was allowed to dry for a minimum of 10 minutes. Epoxy adhesive was used to adhere the two end caps (Arcor Inc.; Chicago, Ill.) in place and the adhesive was allowed to dry overnight prior to using the cartridge for extracting water.

| Cartridge Characteristics | |
|---|---|
| active particles | ATS |
|  | Anex |
| Membrane Thickness | |
| ATS | 2.2 mm |
| Anex | 2.4 mm |
| linear membrane length | |
| ATS | 40.6 cm |
| Anex | 40.6 cm |
| membrane width | |
| ATS | 17 cm |
| Anex | 17 cm |
| total particle content | |
| ATS | 76.1 grams |
| Anex | 61.4 grams |
| water extraction properties | |
| flow rate across cartridge | 3.8 L/min |
| target analytes | |
| ATS | $Sr^{+2}$ |
| Anex | $ReO_4^{-1}$ |
| analyte feed concentrations | |
| $Sr^{+2}$ | 1.0 ppm |
| $ReO_4^{-1}$ | 3.0 ppm |
| See Table 1, below, for data. | |
| linear membrane length | |
| ATS | 40.6 cm |
| Anex | 40.6 cm |
| membrane width | |
| ATS | 17 cm |
| Anex | 17 cm |
| total particle content | |
| ATS | 76.1 grams |
| Anex | 61.4 grams |
| Water Extraction Conditions | |
| flow rate across cartridge | 3.8 L/min |
| target analytes | |
| ATS | $Sr^{+2}$ |
| Anex | $ReO_4^{-1}$ |
| analyte feed concentrations | |
| $Sr^{+2}$ | 1.0 ppm |
| $ReO_4^{-1}$ | 3.0 ppm |
| See Table 1, below, for data. | |

TABLE 1

| | Cartridge Styles | | | | | |
|---|---|---|---|---|---|---|
| | Pleated* | | Spiral without scrim | | Spiral with scrim | |
| Example # | back pressure (Pascals) | **capacity at 50% breakthrough | back pressure (Pascals) | capacity at 50% breakthrough | back pressure (Pascals) | capacity at 50% breakthrough |
| 1 | 0.00029 | 129 | 0.00275 | 278 | — | — |
| 2 | 0.00029 | 15 | 0.00073 | 42 | — | — |
| 3 | — | — | 0.00275 | 278 | 0.00160 | 394 |
| 4 | — | — | 0.00392 | 250 | 0.00189 | 248 |
| 5 | — | — | 0.00435 | 22 | 0.00174 | 35 |
| 6 | — | — | 0.00174 | 0.9 | 0.00073 | 1.3 |
| 7 | — | — | — | — | 0.00189 | 1.0 |
| 8 | — | — | 0.00247 | 44 | 0.00116 | 78 |
| 9 | — | — | 0.00116 | 0.6 | 0.00087 | 3.2 |
| 10 | — | — | 0.00029 | 142 | 0.00022 | 178 |
| 11 | — | — | 0.00029 | 1.5 | 0.00022 | 2.0 |
| 12† | — | — | — | — | 0.00170 | $Sr^{+2}$ - 2.8 $ReO_4^{-1}$ - 130 |
| 13† | — | — | — | — | 0.00156 | $Sr^{+2}$ - 27.6 $ReO_4^{-1}$ - 23 |

Note:
*comparative
**capacity units are (milligrams of analyte/gram of active particle)
†perrhenate capacity calculated at 10% breakthrough for Examples 12 and 13.

The data of Table 1 show the higher extraction efficiency of spirally wound cartridges (without scrim) compared to pleated cartridges. Also, the data of Table 1 show the superior properties of lower back pressure and higher capacity at 50% breakthrough (i.e., higher extraction efficiency) of spirally wound cartridges with scrim compared to spirally wound cartridges without scrim.

Various modifications and alterations which do not depart from the scope and spirit of this invention will become apparent to those skilled in the art. This invention is not to be unduly limited to the illustrative embodiments set forth herein.

We claim:

1. A method for removing an analyte from a fluid comprising the steps:
   a) providing a device for removing an analyte from a fluid containing the analte, the device comprising:
      1) a hollow core comprising a tubular structure having an internal cavity an outer surface, fluid inlet openings from the outer surface into said cavity and a fluid outlet; and
      2) a layered sheet composite comprising:

i) a porous membrane comprising a fibrous sheet material having analyte-sorbing particles enmeshed therein capable of removing the analyte from the fluid; and ii) a porous reinforcing spacer sheet, the layered sheet being formed into a spiral configuration with the porous reinforcing spacer sheet being disposed over the outer surface and inlet openings of the core and being interposed between adjacent overlapping portions of the porous membrane; and b) passing the fluid containing the analyte through the spirally wound sheet composite essentially normal to a surface of the sheet composite so as to bind the analyte to the particulate of the particulate-loaded porous membrane.

2. The method according to claim 1 wherein said porous membrane of said sheet composite is selected from the group consisting of nonwoven or woven sheet materials, wet-laid fibrous pulp webs, and solid sheets with pores therein.

3. The method according to claim 1 wherein said particulate is selected from the group consisting of particles that bind by ion exchange, chelation, covalent bond formation, size exclusion, and sorption.

4. The method according to claim 3 wherein said particulate comprises a hydrophobic zeolite.

5. The method according to claim 1 wherein said sheet composite further comprises inactive diluent particles.

6. The method according to claim 1 wherein said reinforcing and spacer sheet is selected from the group consisting of screens and scrims.

7. The method according to claim 1 wherein said fluid enters said device essentially normal to the spirally wound layered sheet composite and exits through said fluid outlet.

8. The method according to claim 1 wherein said fluid enters said device through the fluid outlet and exits through said spirally wound layered sheet composite.

9. The method according to claim 1 further comprising the step of eluting said bound analyte from said sheet composite with a stripping solution.

10. A device for removing an analyte from a fluid containing the analyte, said device comprising a) a hollow core comprising a tubular structure having an internal cavity, an outer surface, fluid inlet openings from said outer surface into said cavity and a fluid outlet; and b) a layered sheet composite comprising 1) a porous membrane comprising a fibrous sheet material having analyte-sorbing particles enmeshed therein capable of removing said analyte from said fluid; and 2) a porous reinforcing spacer sheet, said layered sheet being formed into a spiral configuration with said porous reinforcing spacer sheet being disposed over said outer surface and inlet openings of said core; and being interposed between adjacent overlapping portions of said porous membrane.

11. The device according to claim 10 wherein said porous membrane comprises a fibrillated polytetrafluoroethylene web.

12. The device according to claim 10 wherein said porous membrane comprises a nonwoven web.

13. The device according to claim 12 wherein said nonwoven web comprises blown microfibers.

14. The device according to claim 10 wherein said porous membrane comprises a wet-laid mat.

15. The device according to claim 10 wherein said particulate is selected from the group consisting of activated carbon, inorganic oxide or derivatives thereof, styrene divinylbenzene or derivatives thereof, ion exchange resins, and chitin.

16. The device according to claim 10 wherein said particulate is selected from the group consisting of particles that bind by ion exchange, chelation, covalent bond formation, size exclusion, and sorption.

17. The device according to claim 10 wherein said particulate is an inorganic oxide having organic moieties bonded thereto.

18. The device according to claim 10 wherein said reinforcing spacer sheet is a screen or scrim.

19. The device according to claim 18 wherein said screen is selected from the group consisting of polymeric, glass, and metal screens.

20. The device according to claim 19 wherein said scrim is selected from the class consisting of polymeric, glass, and metal scrims.

21. The device according to claim 10 wherein said spirally wound sheet composite is enclosed within a porous protective sheath.

* * * * *

UNITED STATES PATENT AND TRADEMARK OFFICE
CERTIFICATE OF CORRECTION

PATENT NO. : 5,897,779
DATED : April 27, 1999
INVENTOR(S) : Eric E. Wisted and Susan H. Lundquist It is certified that error appears in the above-identified patent and that said Letters Patent is hereby corrected as shown below:

Column 10,
Line 27, please delete "PJTFE" and insert -- PTFE --.

Column 16,
Line 42, "Carbon", please insert before "Keystone" -- ( --.

Column 18,
Line 42, after "Carbon", please insert before "Norit" -- ( --.

Column 20,
Line 62, please delete "analte" and insert -- analyte --.

Signed and Sealed this

Thirtieth Day of April, 2002

Attest:

Attesting Officer

JAMES E. ROGAN
Director of the United States Patent and Trademark Office